United States Patent
Kang et al.

(10) Patent No.: US 10,078,209 B1
(45) Date of Patent: Sep. 18, 2018

(54) OPTIC ASSEMBLY AND LIGHT SOURCE DEVICE FOR ENDOSCOPE INCLUDING THE SAME

(71) Applicant: INTHESMART Inc., Seoul (KR)

(72) Inventors: Uk Kang, Seoul (KR); Ilhyung Shin, Jeju (KR)

(73) Assignee: INTHESMART INC., Seoul (KR)

( * ) Notice: Subject to any disclaimer, the term of this patent is extended or adjusted under 35 U.S.C. 154(b) by 0 days.

(21) Appl. No.: 15/648,414

(22) Filed: Jul. 12, 2017

(30) Foreign Application Priority Data

May 10, 2017 (KR) .......................... 10-2017-0057982

(51) Int. Cl.
*G01S 13/78* (2006.01)
*G02B 23/24* (2006.01)
*G02B 23/04* (2006.01)

(52) U.S. Cl.
CPC ......... *G02B 23/2461* (2013.01); *G02B 23/04* (2013.01); *G02B 23/2423* (2013.01)

(58) Field of Classification Search
None
See application file for complete search history.

(56) References Cited

U.S. PATENT DOCUMENTS

| 5,914,802 A * | 6/1999 | Stappaerts ........ G02F 1/133553 |
| | | 359/276 |
| 2011/0019285 A1* | 1/2011 | Kuo ................... G02B 27/0025 |
| | | 359/637 |

* cited by examiner

*Primary Examiner* — Elmito Breval
(74) *Attorney, Agent, or Firm* — Patent Office of Dr. Chung Park

(57) ABSTRACT

Disclosed is an optical assembly including: a case provided with a first optical path, which passes light from a first light source, and a second optical path, which communicates with a side of the first optical path and introduces the light from a second light source into the first optical path; and a beam splitter that divides the first optical path into an irradiation area in a front side and an incident area in a rear side, maintains a traveling direction with respect to the light irradiated from the first light source, and changes the traveling direction of the light from the second light source so that the light from the second light source can travel parallel to the light irradiated from the first light source. The centerline of the irradiation area and a centerline of the incidence area are not parallel to each other.

7 Claims, 9 Drawing Sheets

[Fig. 1]
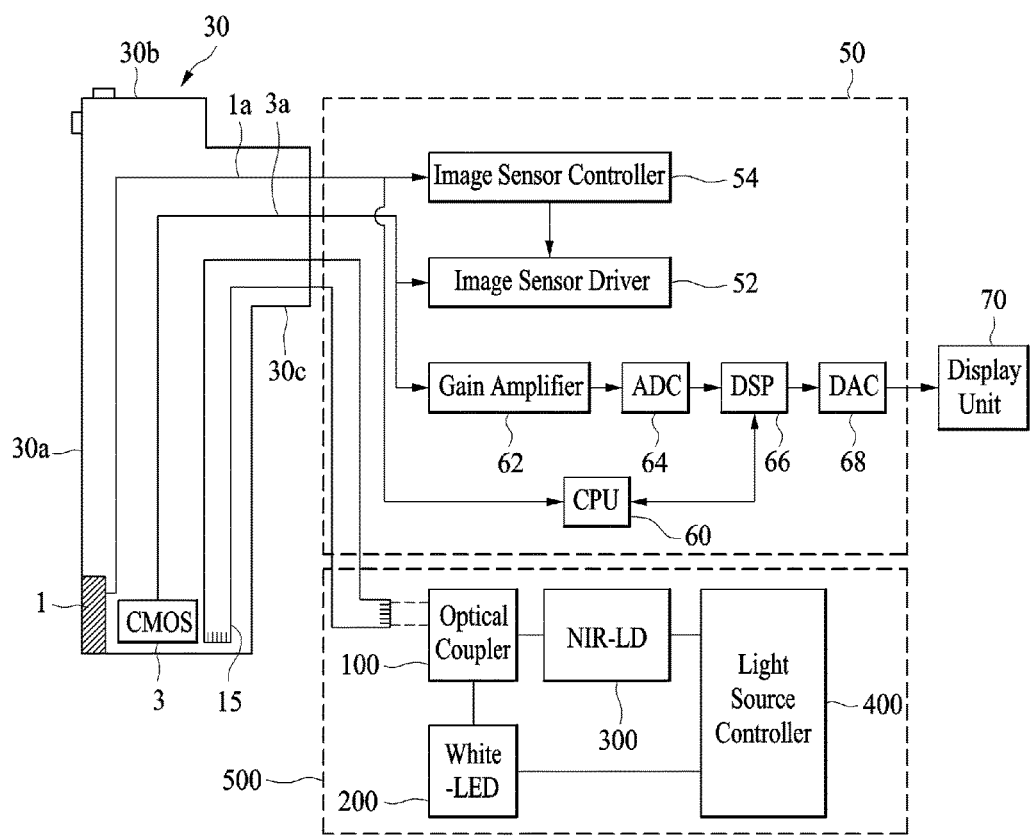

[Fig. 2]
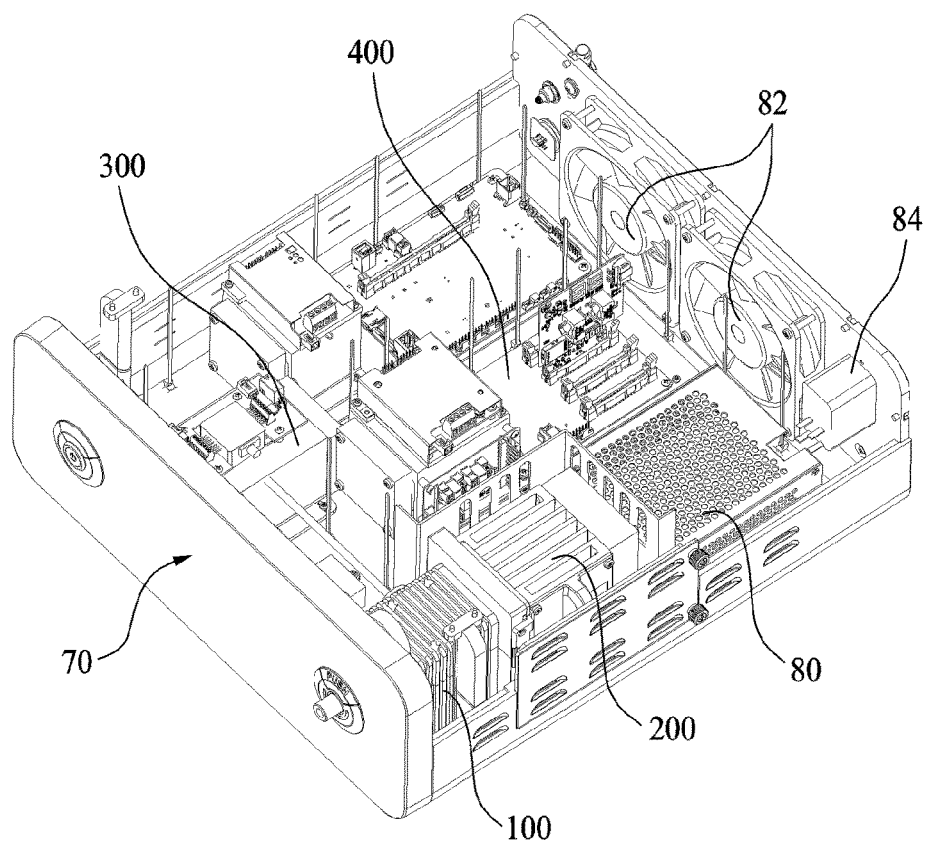

[Fig. 3]
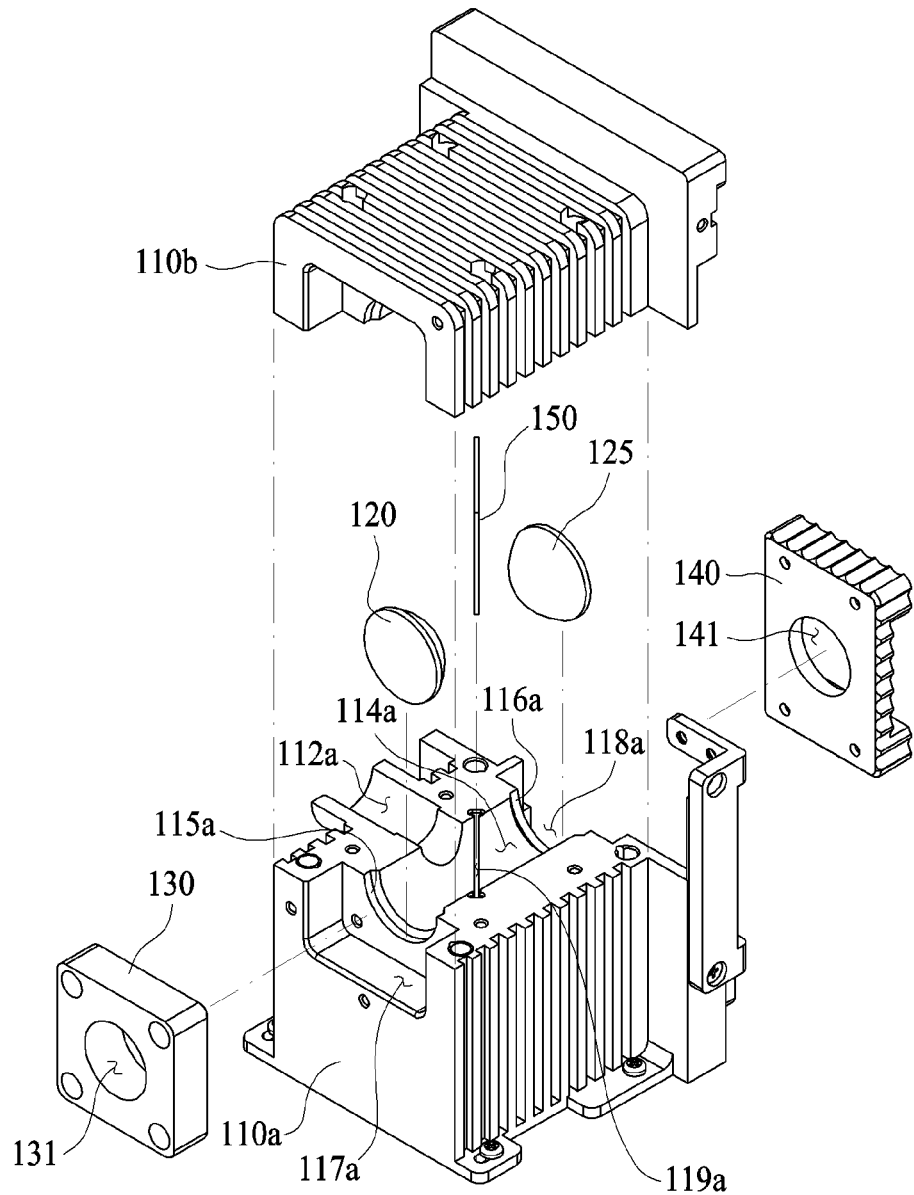

[Fig. 4]
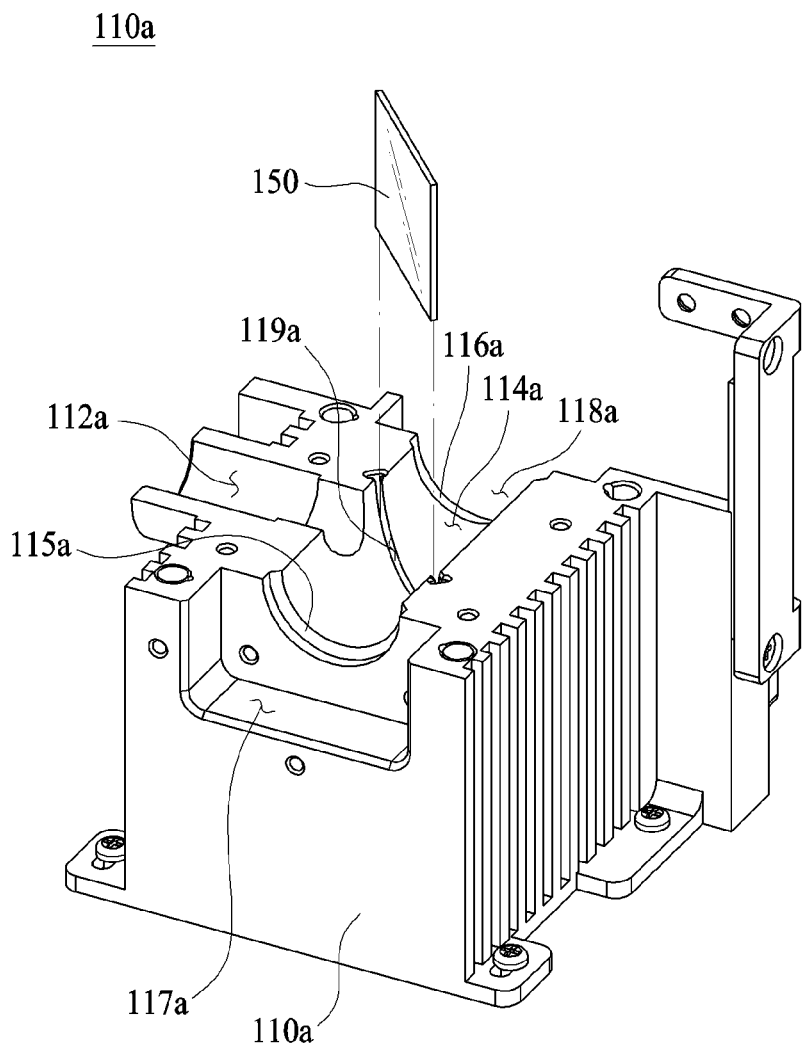

[Fig. 5]
110b
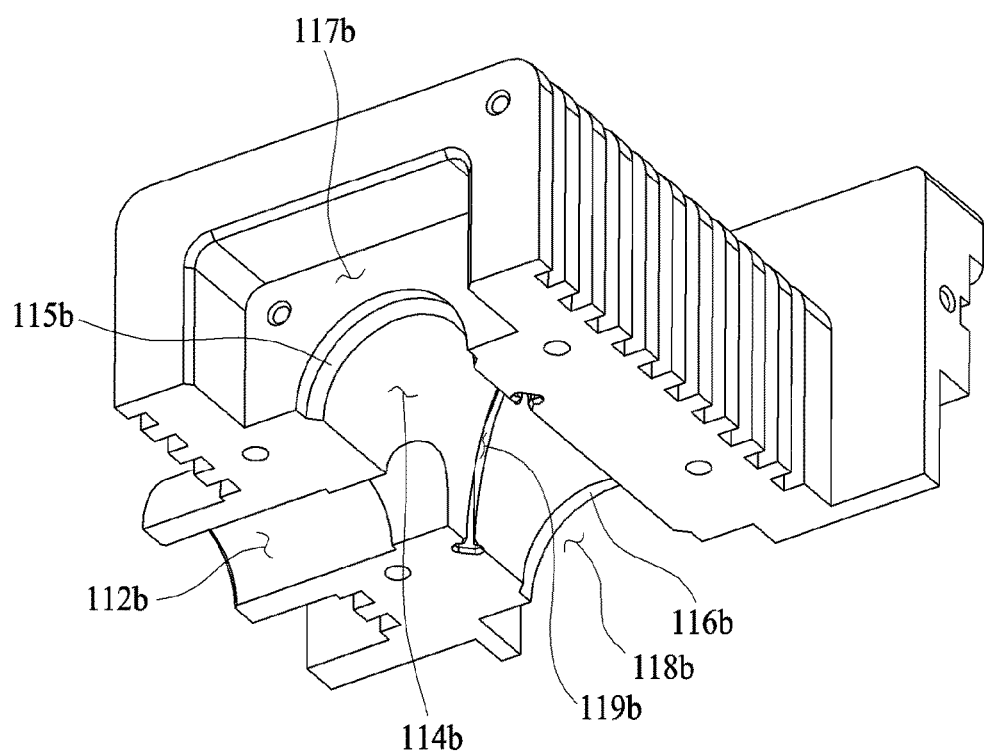

[Fig. 6]
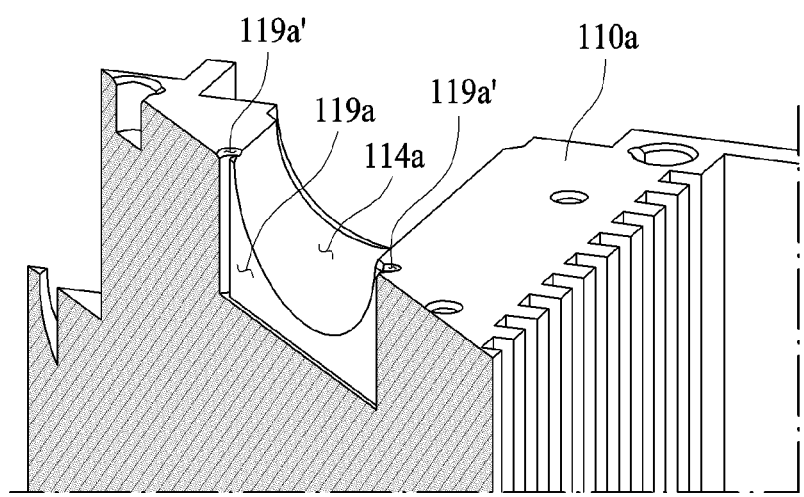

[Fig. 7]
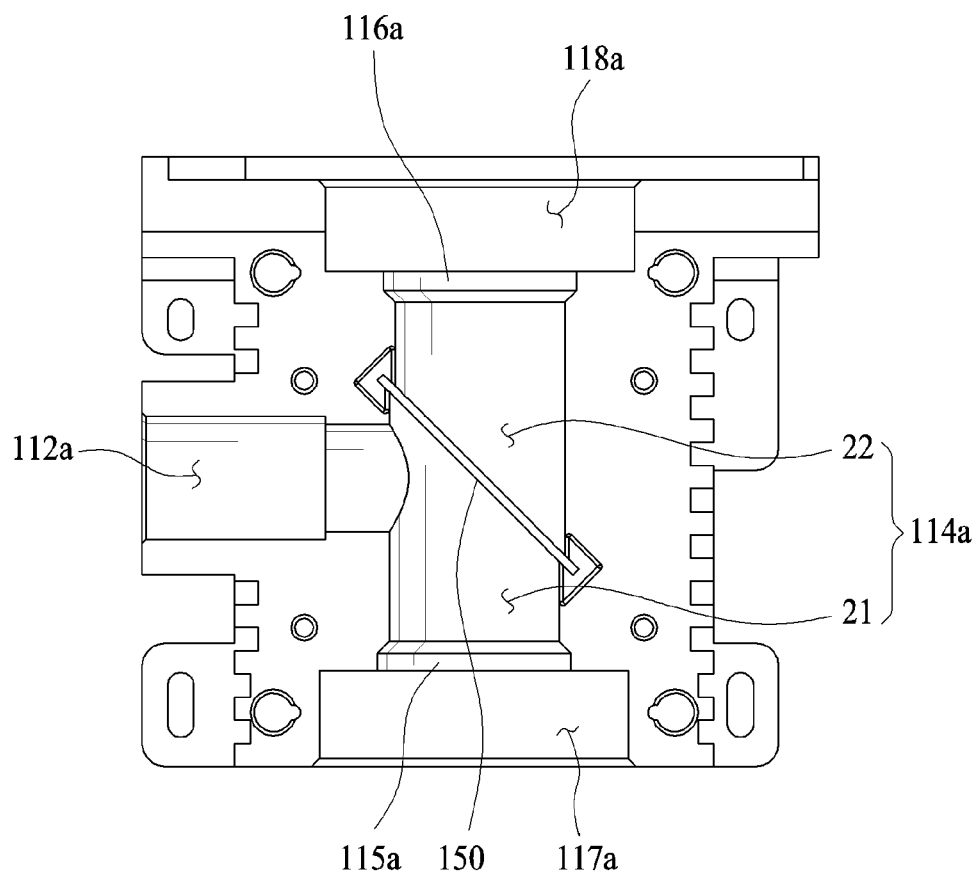

[Fig. 8]
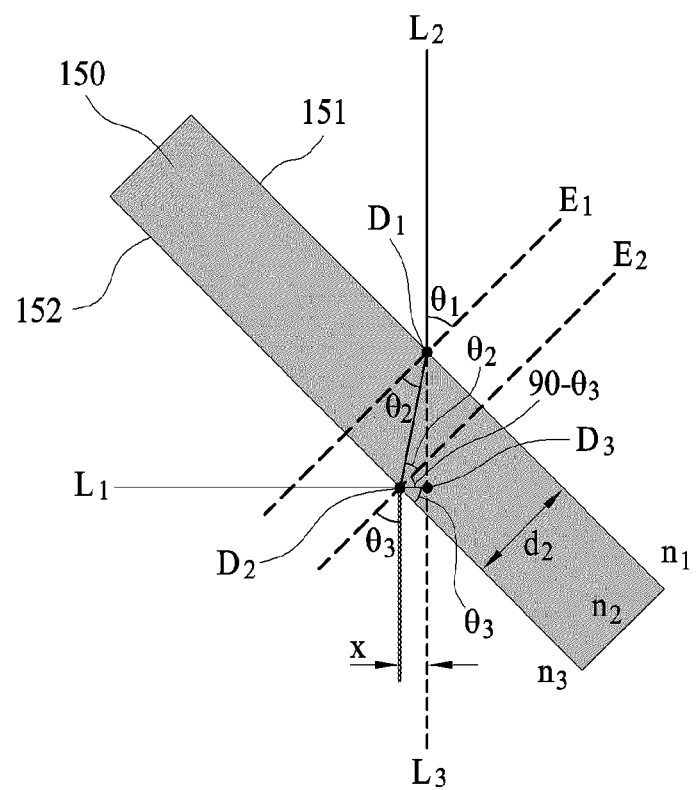

[Fig. 9]
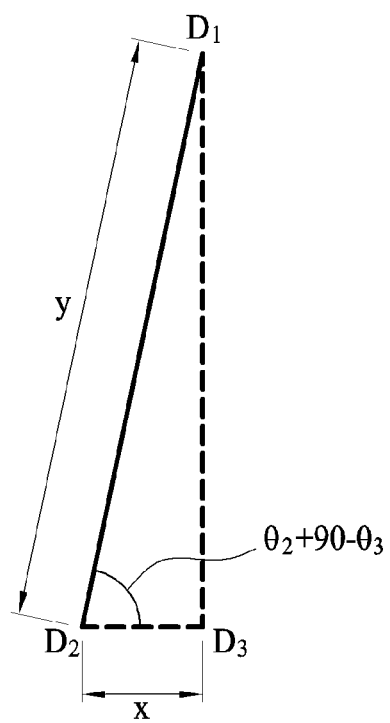

OPTIC ASSEMBLY AND LIGHT SOURCE DEVICE FOR ENDOSCOPE INCLUDING THE SAME

CROSS-REFERENCE TO RELATED APPLICATIONS

This application claims priority under 35 U.S.C. § 119 from Korean Application No. 10-2017-0057982 filed on May 10, 2017, the subject matter of which is incorporated herein by reference.

BACKGROUND OF THE INVENTION

Field of the Invention

The present invention relates to an optical assembly and a light source device for endoscope including the same, and more particularly, to an optical assembly which is formed in such a manner that a center line of an irradiation area located at the front side and a center line of an incident area located at the rear side are not identical with each other based on a beam splitter so that a traveling trace of light irradiated from a first light source and a traveling trace of light irradiated from a second light source in a different direction from the first light source are not parallel to each other, and a light source device for endoscope including the same

Description of the Related Art

An endoscope is a device that can capture an image and monitor narrow spaces such as the inside of a human body and the inside of a machine. It can be used not only in a medical field, but also in various industrial fields such as monitoring the inside of a precision machine without disassembling and monitoring abnormality in the inside of a pipe.

Particularly, in the medical field, the endoscope can monitor the inside of a human body (stomach, bronchus, esophagus, large intestine, small intestine, etc.) by using a small-sized camera without the ventrotomy or incision of body such as surgery or autopsy, or by passing through a part of body to monitor the inside of the abdominal cavity such that it can check whether any abnormal exists.

A well-known conventional endoscope system includes, in a fore-end of the endoscope, a light source device for irradiating light to view the internal organs of body or the inside surface of a machine, an image sensor for receiving a light signal which is irradiated from the light source device is reflected from the surface of internal organ of human body after being projected and converting the received light signal into an electrical signal (image signal), and a camera with a camera chip including an encoder for converting the image signal into an electronic signal so that the image signal can be monitored through a monitor.

Meanwhile, with the development of medical technology, an endoscopy through near-infrared rays as well as endoscopy through visible light is often performed. However, in the conventional case, since two types of light can not be simultaneously transmitted through a single endoscope, a separate check-up had to be carried out to accomplish two types of endoscopy.

This increases the time required for the operation, and further requires an additional effort by the operator and additional treatment costs, which also causes a patient to suffer pain due to repetitive procedures.

In addition, even if two types of light are simultaneously irradiated, since it is very difficult to accurately irradiate two types of light to a correct operation site, such attempts have not been made until now.

Accordingly, a method for solving such problems is required.

SUMMARY OF THE INVENTION

The present invention has been made in view of the above problems, and provides an optical assembly capable of simultaneously accomplishing multiple check-ups by transmitting a plurality of types of light through a single endoscope, and a light source device for endoscope including the optical assembly.

Thus, it is possible to reduce the time required for the operation and the cost of the operation, and to minimize the effort and suffering of patient and operator.

In accordance with an aspect of the present invention, an optical assembly includes: a case provided with a first optical path, formed therein, which passes light irradiated from a first light source, and a second optical path, formed therein, which communicates with a side of the first optical path and introduces the light irradiated from a second light source in a different direction from the first light source into the first optical path; and a beam splitter provided in the first optical path, divides the first optical path into an irradiation area in a front side and an incident area in a rear side, maintains a traveling direction with respect to the light irradiated from the first light source, and changes the traveling direction of the light irradiated from the second light source so that the light irradiated from the second light source can travel is parallel to the light irradiated from the first light source, wherein the first optical path is formed in such a manner that a centerline of the irradiation area and a centerline of the incidence area are not parallel to each other.

The centerline of the irradiation area and the centerline of the incidence area are laterally spaced by a preset correction distance (x) so that a traveling trace of the light irradiated from the first light source and a traveling trace of the light irradiated from the second light source coincide with each other in the irradiation area.

The correction distance is calculated by following equation $$x = \frac{d_2}{\cos\theta_2} \cdot \cos(\theta_2 + 90 - \theta_3)$$

($d_2$: a thickness of beam splitter)

($\theta_2$: an angle between a first vertical line passing through a first contact point where the light irradiated from the first light source meets a rear surface of the beam splitter and perpendicular to the rear surface of the beam splitter and a trace of the light, irradiated from the first light source, travelling in the beam splitter)

($\theta_3$: an angle between a second vertical line passing through a second contact point where the light irradiated from the first light source meets a front surface of the beam splitter and perpendicular to the front surface of the beam splitter and a trace of the light, irradiated from the first light source, travelling in the beam splitter)

An insertion groove corresponding to a cross-sectional shape of the beam splitter is formed on an inner circumferential surface of the first optical path formed in the case, so that the beam splitter is inserted and fixed to the insertion groove.

The case includes an upper case and a lower case divided to bisect the first optical path, the second optical path, and the insertion groove.

The case includes a first lens coupling unit formed in a front end of the first optical path and a second lens coupling unit formed in a rear end of the first optical path, and the optical assembly further includes a first lens coupled to the first lens coupling unit and a second lens coupled to the second lens coupling unit.

BRIEF DESCRIPTION OF THE DRAWINGS

The objects, features and advantages of the present invention will be more apparent from the following detailed description in conjunction with the accompanying drawings, in which:

FIG. 1 is a diagram illustrating a schematic configuration of an endoscope system according to the present invention;

FIG. 2 is a diagram illustrating an internal structure of a light source device applied to an endoscope system of the present invention;

FIG. 3 is a diagram illustrating a structure of an optical assembly, in a light source device applied to an endoscope system according to an embodiment of the present invention;

FIG. 4 is a diagram illustrating a lower case of an optical assembly, in a light source device applied to an endoscope system according to an embodiment of the present invention;

FIG. 5 is a diagram illustrating an upper case of an optical assembly, in a light source device applied to an endoscope system according to an embodiment of the present invention;

FIG. 6 is a diagram illustrating a structure of an insertion groove, in a light source device applied to an endoscope system according to an embodiment of the present invention;

FIG. 7 is a detailed diagram illustrating a structure of a first optical path, in a light source device applied to an endoscope system according to an embodiment of the present invention;

FIG. 8 is a diagram illustrating a traveling trace of light by a beam splitter, in a light source device applied to an endoscope system according to an embodiment of the present invention; and FIG. 9 is a diagram illustrating a process of calculating a correction distance between a center line of an irradiation area of a first optical path and a center line of an incident area, in a light source device applied to an endoscope system according to an embodiment of the present invention.

DETAILED DESCRIPTION OF EXEMPLARY EMBODIMENTS

Exemplary embodiments of the present invention are described with reference to the accompanying drawings in detail. The same reference numbers are used throughout the drawings to refer to the same or like parts. Detailed descriptions of well-known functions and structures incorporated herein may be omitted to avoid obscuring the subject matter of the present invention.

FIG. 1 is a diagram illustrating a schematic configuration of an endoscope system according to the present invention.

Referring to FIG. 1, the endoscope system according to an embodiment of the present invention may include a light source device 500, an image processing device 50, an electronic endoscopes 30 (hereinafter, referred to as an endoscope 30), an image display device 70, and an input device (not shown).

The light source device 500 may be provided with a combined white-NIR illuminator including a first light source assembly 200 and a second light source assembly 300 to obtain information such as biological characteristics from an object (e.g., the internal organs of the human body) to be monitored, and transmit a light irradiated from them to the endoscope 30. In the present embodiment, it is assumed that the first light source assembly 200 irradiates a white light and the second light source assembly 300 irradiates a near-infrared ray. However, the light irradiated from the first light source assembly 200 and the second light source assembly 300 is not limited thereto.

The image processing device 50 may control an image processing of the endoscope 30 and perform an image signal processing on an image obtained by the endoscope 30.

The endoscope 30 may be electrically detachably connected to the image processing device 50, and may be optically coupled to the light source device 500 through an optical cable. The white light or the near infrared ray excitation light transmitted from the light source device 500 may be irradiated to the inside of human body, and the visible light reflected from an object, the near infrared ray excitation light, and the fluorescence caused by the near infrared ray excitation light may be monitored as an image by a built-in image sensor. At this time, the image sensor may convert the captured image into an image signal.

The image display device 70 and the input device may be connected to the image processing device 50. The image display device 70 may be implemented of an LCD capable of displaying the generated image or any other form capable of displaying an image as such. The input device may include a form capable of inputting various types of information of transmittable signal to the image processing device 50 or the image display device 70 such as an input button provided in the endoscope 30, or a keyboard or a mouse which is separately provided.

The endoscope 30 capable of monitoring the visible light irradiated from a monitoring target or the light in a near infrared ray excitation light area may include a flexible or rigid insertion unit 30a inserted into a body cavity in which light hardly reaches, an operation unit 30b provided at the end of the insertion unit 30a, and a universal cord unit 30c extending from the side of the operation unit 30b, and electrically connected to the image processing device 50 through the universal cord unit 30c.

A main body unit of the endoscope 30 may mainly include the insertion unit 30a and the operation unit 30b, and the captured image signal and control signals may be transmitted to the image processing device 50 through a cable 3a.

An image sensor 3 forceps hole may be provided in a distal end of the insertion unit 30a. Since the forces hole is well known to those skilled in the art, a detailed description is omitted. In addition to the forceps holes which can be applied to a hard endoscope, it is obvious that air/water tube hole, biopsy channel hole, and the like which can be applied to a flexible endoscope may be applied.

The image sensor 3 may be electrically connected to an image sensor driver 52 through the cable 3a bundled with a plurality of signal wires.

A light guide 15 may be connected to the light source unit 500 through the universal cord unit 30c in the insertion unit 30a. The light guide 15 may include an optical system (not shown), and may guide a compound light source provided by the light source device 500, that is, a white light source and a near infrared ray excitation light to be output to the end of the insertion unit.

The image processing device 50 may include an image sensor controller 54, an image sensor driver 52, a gain amplifier 62, an analog-to-digital converter (ADC) 64, a digital signal processor (DSP) 66, and a digital-to-analog converter (DAC) 68.

The image sensor driving unit 52 may drive an image sensor 3 built in the endoscope 30, and may be controlled in such a manner that a control input through the image sensor controller 54 is processed by a CPU 60.

The gain amplifier 62 may perform gain control for the image signal generated by an image pickup device 1 and the image sensor 3, and the analog-to-digital converter 64 may convert the image signal into a digital signal.

The digital signal processor 66 may perform various types of image processing such as image synthesis and white balancing for the digital image signal.

In addition, the digital signal processor 66 may adjust the image processing timing in cooperation with the CPU 60.

The digital-to-analog converter 68 may perform a process for displaying image data, for example, an analog process, and output the image data to the image display device 70.

The light source device 500 connected to the light guide 15 may include an optical assembly (Optical Coupler) 100, the second light source assembly (NIR-LD) 300, the first light source assembly (White-LED) 200, and a light source controller 400. A detailed structure of the light source device 500 is described with reference to FIG. 2.

FIG. 2 is a diagram illustrating an internal structure of the light source device 500 applied to an endoscope system of the present invention.

As described above, the light source device 500 may include the optical assembly 100, the first light source assembly 200, the second light source assembly 300, and the light source controller 400.

These elements may be housed in a housing of the light source device 500. On the inner side of the rear panel of the housing, at least one cooling fan 82 may be disposed to dissipate a heat generated in the components in the housing, and an adapter 84 plugged for the application of an external alternating current (AC) power may be disposed.

A direct current power supply 80 may be disposed inside the housing to be adjacent to the adapter 84 and convert the alternating current (AC) power applied to the adapter 84 into a direct current (DC) power.

The optical assembly 100 is an element which collects optical signals transmitted from the first light source assembly 200 and the second light source assembly 300 and transmits the collected optical signals to the endoscope side. Here, the first light source assembly 200 and the second light source assembly 300 may be controlled by the light source controller 400.

In addition, as described above, in the present embodiment, it is assumed that the first light source assembly 200 irradiates a white light and the second light source assembly 300 irradiates a near infrared ray. However, the light irradiated from the first light source assembly 200 and the second light source assembly 300 is not limited thereto.

Meanwhile, the light source device 500 according to the embodiment of the present invention may include an electrostatic touch assembly 70 for controlling each light source through an operation. The electrostatic touch assembly 70 may perform quick and accurate input by applying an electrostatic touch method, and may prevent a malfunction and a breakdown due to various electric outbreak situations fundamentally. In addition, the light source control method of the light source device 500 is not limited to the electrostatic touch method, and it is obvious that any method for controlling the light source can be applied.

Hereinafter, the optical assembly 100 is described in detail.

FIG. 3 is a diagram illustrating a structure of the optical assembly 100, in a light source device applied to an endoscope system according to an embodiment of the present invention, FIG. 4 is a diagram illustrating a lower case 110a of the optical assembly 100, in a light source device applied to an endoscope system according to an embodiment of the present invention, and FIG. 5 is a diagram illustrating an upper case 110b of an optical assembly 100, in a light source device applied to an endoscope system according to an embodiment of the present invention.

As shown in FIGS. 3 to 5, the optical assembly 100 includes a case 110a and 110b, a beam splitter 150 coupled to the inside of the case 110a and 110b, a first lens 120, a second lens 125, a first shielding block 130, and a second shielding block 140.

The case 110a and 110b include an upper case 110b and a lower case 110a and are formed to divide a first light path 114a and 114b and a second light path 112a and 112b formed inside the case 110a and 110b into two parts.

At this time, the first optical path 114a and 114b which passes the light irradiated from the first light source, and a second optical path 112a and 112b which communicates with the side of the first optical path 114a and 114b and which introduces the light irradiated from the second light source in the different direction from the first light source into the first optical path 114a and 114b may be formed in the inside of the case 110a and 110b.

The first optical path 114a and 114b may form a path for passing the light irradiated from the first light source of the first light source assembly 200 (see FIG. 3) provided in the rear side of the optical assembly 100. In the present embodiment, the first optical path 114a and 114b may be formed to be directed to the front side from the rear side of the case 110.

In addition, the second optical path 112a and 112b may be extended in the vertical direction from the middle point of the first optical path 114a and 114b, and may form a path for passing the light irradiated from the second light source of the second light source assembly 300 (see FIG. 2) provided in one side of the optical assembly 100. That is, the light irradiated through the second optical path 112a and 112b may reach a confluence point of the first optical path 114a and 114b and the second optical path 112a and 112b.

At this time, the beam splitter 150 may be provided adjacent to the first optical path 114a and 114b, specifically, the confluence point of the first optical path 114a and 114b and the second optical path 112a and 112b.

The beam splitter 150 may maintain the traveling direction with respect to the light irradiated from the first light source, and may change the direction of the light irradiated from the second light source so that the light irradiated from the second light source travels in the same direction as the light irradiated from the first light source. That is, the light irradiated from the first light source and the light irradiated from the second light source may be irradiated from a different direction. However, they may be diverted to the same direction by the beam splitter 150 and transmitted to the endoscope side.

As the beam splitter 150, a dichronic mirror or the like may be applied, and in addition, it is obvious that various optical mirrors may be used.

Particularly, in the present embodiment, an insertion groove 119a and 119b, corresponding to a cross-sectional shape of the beam splitter 150, may be formed on the inner circumferential surface of the first optical path 114a and 114b so that the beam splitter 150 may be inserted and fixed to the insertion groove.

The insertion groove 119a and 119b may be formed adjacent to the confluence point of the first optical path 114a and 114b and the second optical path 112a and 112b and the first optical path 114a and 114b, and may be formed in an oblique direction with respect to each of the first optical path 114a and 114b and the second optical path 112a and 112b to fix the beam splitter 150.

In addition, in the present embodiment, the case 110 may include a first lens coupling unit 115a and 115b which is formed in the front end of the first optical path 114a and 114b, and a second lens coupling unit 116a and 116b which is formed in the rear end of the first optical path 114a and 114b. Thus, a first lens 120 may be coupled to the first lens coupling unit 115a and 115b, and a second lens 125 may be coupled to the second lens coupling unit 116a and 116b.

The first lens 120 and the second lens 125 may determine the transmittance of light according to the optical characteristic. In the present embodiment, the first lens 120 and the second lens 125 may be formed in such a manner that one surface is flat and the other surface is manufactured in a protruding shape, and the other surface faces toward the beam splitter 150 side. At this time, the first lens coupling unit 115a and 115b and the second lens coupling unit 116a and 116b may have a step corresponding to a circumference surface shape of the first lens 120 and the second lens 125 so that the first lens 120 and the second lens 125 may be stably mounted.

In addition, in the present embodiment, the optical assembly 100 may further include a first shielding block 130 coupled to the case 110 so as to shield the front of the first lens coupling unit 115a and 115b, and a second shielding block 140 coupled to the case 110 so as to shield the rear of the second lens coupling unit 116a and 116b.

The first shielding block 130 and the second shielding block 140 may prevent the first lens 120 and the second lens 125 from being detached to the outside of the case 110. In detail, a first shielding block 130 may be fastened to a first block coupling unit 117a and 117b formed in the front end of the case 110, and a second shielding block 140 may be fastened to a second block coupling unit 118a and 118b formed in the rear end of the case 110.

Particularly, the first shielding block 130 and the second shielding block 140 may be provided with through holes 131 and 141 through which light can pass respectively. The diameter of the through holes 131 and 141 may be formed smaller than the first lens 125 and the second lens 125. This is to prevent the first lens 120 and the second lens 125 from being detached through the through holes 131 and 141.

FIG. 6 is a diagram illustrating a structure of an insertion groove 119a and 119b, in a light source device applied to an endoscope system according to an embodiment of the present invention.

As shown in FIG. 6, the insertion groove 119a and 119b may be formed in an oblique shape on the first optical path 114a and have a cross section corresponding to the shape of the beam splitter 150.

In the present embodiment, since the beam splitter 150 is formed in a rectangular shape, the insertion groove 119a and 119b is also formed in a rectangular shape having a size corresponding to the beam splitter 150 in a state where the upper case 110b and the lower case 110a is coupled to each other.

Thus, the lower portion of the beam splitter 150 may be inserted into the insertion groove 119a of the lower case 110a while the upper case 110b and the lower case 110a are separated from each other. Then, the insertion groove 119a of the upper case 110b may be fitted into the upper portion of the beam splitter 150 such that the upper case 110b and the lower case 110a may be coupled to each other.

As described above, according to the present invention, the beam splitter 150 can be easily combined and separated as the case 110a, 110b is divided into the upper case 110b and the lower case 110a, which is advantageous for maintenance and replacement.

Meanwhile, in the present embodiment, an auxiliary groove 119a' protruding in the thickness direction of the insertion groove 119a and 119b may be formed in both ends of the insertion groove 119a and 119b, so that the beam splitter 150 can be easily inserted.

In addition, when an auxiliary guide (not shown) having a corresponding shape is formed in both ends of the beam splitter 150 so as to be inserted into the auxiliary groove 119a', the beam splitter 150 can be fixed to the insertion groove 119a and 119b more stably without shaking.

On the other hand, as shown in FIG. 7, the beam splitter 150 divides the first optical path 114a and 114b into two areas of the front and rear sides. In the present embodiment, the front area of the first optical path 114a and 114b is referred to as an irradiation area 21, and the rear area thereof is referred to as an incident area 22.

In the incidence area 22, the light irradiated from the first light source is introduced and travels toward the beam splitter 150. In addition, in the irradiation area 21, the light, which has passed through the beam splitter 150, irradiated from the first light source 150 and the light irradiated from the second light source reflected by the beam splitter 150 travel forward.

At this time, the light irradiated from the first light source is refracted during the process of passing through the beam splitter 150, so that the traveling trace in the incident area 22 and the traveling trace in the irradiation area 21 are not parallel to each other.

Therefore, in the present embodiment, the first optical path 114a and 114b are formed in such a manner that the center line of the irradiation area 21 and the center line of the incident area 22 are not parallel to each other along the traveling trace of the light irradiated from the first light source.

Particularly, in the present embodiment, as shown in FIG. 8, the centerline of the irradiation area 21 and the centerline of the incident area 22 may be laterally spaced by a preset correction distance (x) so that the traveling trace of the light irradiated from the first light source and the traveling trace of the light irradiated from the second light source coincide with each other in the irradiation area 21.

That is, the correction distance x between the center line of the irradiation area 21 and the center line of the incident area 22 can be set in consideration of the refraction of the light irradiated from the first light source, and this can be determined in consideration of various factors such as a thickness d2 of the beam splitter 150, a refractive index, a holding angle, and the like.

Hereinafter, the process of calculating the correction distance x between the center line of the irradiation area 21 and the center line of the incident area 22 is described with reference to FIG. 8.

As shown in FIG. 8, the light L2 irradiated from the first light source travels along the center line of the incidence area 22 to form a first contact point D1 with a rear surface 151 of the beam splitter 150, and is refracted from the first contact point D1 to form a second contact point D2 with a front surface 152 of the beam splitter 150. The light L2 irradiated from the first light source is refracted again at the second contact point D2 and travels forward along the center line of the irradiation area 21.

The light L1 irradiated from the second light source is introduced through the above mentioned second optical path 112a and 112b (see FIGS. 4 and 5) to form the second contact point D2 with the front surface 152 of the beam splitter 150. The light L1 irradiated from the second light source is reflected at the second contact point D2 and travels forward along the center line of the irradiation area 21.

That is, the correction distance x between the center line of the irradiation area 21 and the center line of the incident area 22 may be set in order that the traveling traces of the light L2 irradiated from the first light source and the light L1 irradiated from the second light source coincide with each other in the irradiation area 21 by the beam splitter 150.

In other words, this can be regarded as a separation distance between an extension line L3 that extends forwardly the traveling direction of the light L2 irradiated from the first light source in the incident area 22, and the traveling trace of the light L2 irradiated from the first light source and the light L1 irradiated from the second light source in the irradiation area 21.

In order to calculate the correction distance (x), a refractive index is calculated according to the change of medium.

As described above, the light L2 irradiated from the first light source in the incident area 22 forms the first contact point D1 with the rear surface 151 of the beam splitter 150, and is refracted from the first contact point D1.

Here, θ1 indicates an angle between a first vertical line E1 perpendicular to the rear surface 151 of the beam splitter 150 and passing through the first contact point D1 and a trace of the light L2, irradiated from the first light source, travelling in the incident area 22. In addition, θ2 indicates an angle between the first vertical line E1 and a trace of the light L2, irradiated from the first light source, travelling in the beam splitter 150.

In addition, θ3 indicates an angle between a second vertical line E2 perpendicular to the front surface 152 of the beam splitter 150 and passing through the second contact point D2 and a trace of the light L2, irradiated from the first light source, travelling in the irradiation area 21.

Accordingly, based on Snell's law, the following Equation 1 is established.

$$\frac{\sin\theta_1}{\sin\theta_2} = \frac{n_2}{n_1}, \frac{\sin\theta_2}{\sin\theta_3} = \frac{n_3}{n_2} \qquad \text{<Equation 1>}$$

(n1 to n3: absolute refractive index of each medium)

In addition, as shown in FIG. 9, it can be seen that a right triangle is formed by the first contact point D1, the second contact point D2, and the third contact point D3 where an extension line for the trace of the light L2, irradiated from the first light source, traveling in the incidence area 22 and an extension line for the trace of the light L1, irradiated from the second light source, traveling in the second optical path 112a and 112b (see FIGS. 4 and 5) intersect with each other.

At this time, the length of the base of the right triangle shown in FIG. 9 has the same value as the above-described correction distance x.

Here, the length of the hypotenuse of the right triangle, that is, the total length of the trace of the light L2, irradiated from the first light source, traveling in the beam splitter 150 can be calculated through the following Equation 2 based on FIG. 8.

$$y = \frac{d_2}{\cos\theta_2} \qquad \text{<Equation 2>}$$

(d2: thickness of beam splitter)

This is because the angle θ2 between the first vertical line E1 and the trace of the light L2, irradiated from the first light source, travelling in the beam splitter 150 and the angle θ2 between the second vertical line E2 and the trace of the light L2, irradiated from the first light source, travelling in the beam splitter 150 are the same as both angles are alternate angle.

In addition, by using the right triangle in FIG. 9, the relationship between the base and hypotenuse can be summarized as shown in Equation 3 below.

$$\cos(\theta_2 + 90 - \theta_3) = \frac{x}{y} \qquad \text{<Equation 3>}$$

This is because, based on FIG. 8, it can be seen that the angle between the base and the hypotenuse is θ2+90−θ3.

In this case, the angle between the front surface 152 of the beam splitter 150 and the trace of the light L2, irradiated from the first light source, travelling in the irradiation area 21 is 90−θ3. In addition, the angle between the trace of the light L2, irradiated from the first light source, traveling in the irradiation area 21 and the extension line for the trace of the light L1, irradiated from the second light source, traveling in the second optical path 112a and 112b (see FIGS. 4 and 5) is 90°. Therefore, the angle between the extension line for the trace of the light L1, irradiated from the second light source, traveling in the second optical path 112a and 112b and the front surface 152 of the beam splitter 150 is also θ3.

Accordingly, the angle between the second vertical line E2 and the extension line for the trace of the light L1, irradiated from the second light source, traveling in the second optical path 112a and 112b may be defined as 90−θ3.

As a result, the angle between the trace of the light L2, irradiated from the first light source, traveling in the beam splitter 150 and the extension line for the trace of the light L1, irradiated from the second light source, traveling in the second optical path 112a and 112b, that is, the angle between the base and the hypotenuse in the right triangle of FIG. 9 is defined as θ2+90−θ3.

Substituting Equation 2 into Equation 3, the base of the right triangle, i.e., the correction distance x, is expressed by Equation 4 below.

$$x = \frac{d_2}{\cos\theta_2} \cdot \cos(\theta_2 + 90 - \theta_3) \qquad \text{<Equation 4>}$$

Therefore, the first optical path 114a and 114b can be designed in such a manner that the center line of the irradiation area 21 and the center line of the incident area 22 are not parallel to each other by a correction distance x. This may be determined in consideration of various factors such as the thickness d2 of the beam splitter 150, the refractive index, the holding angle, and the like, as described above.

According to the present invention, since a light source device for an endoscope is provided through such a structure, a plurality of types of light can be transmitted through a single endoscope, so that multiple check-ups can be simultaneously performed, and furthermore, the traveling trace of the light irradiated from the first light source and the traveling trace of the light irradiated from the second light source can exactly coincide with each other in the irradiated area.

According to the present invention, the advantages of the optical assembly and the light source device for endoscope including the optical assembly are as follows.

First, as the light source device for endoscope of the present invention is provided, various types of light can be transmitted through a single endoscope, so that a complex check-up can be performed simultaneously.

Second, since the first optical path formed in the housing is implemented in such a manner that the center line of the irradiation area and the center line of the incident area are not parallel to each other, the traveling trace of the light irradiated from the first light source and the traveling trace of the light irradiated from the second light source can exactly coincide with each other in the irradiated area.

Third, the time required for operation and the cost of operation can be significantly reduced.

Fourth, the effort of operator and the suffering of patient can be minimized.

Fifth, since each element can be easily separated from each other, the effort required for maintenance can be minimized.

Hereinabove, although the present invention has been described with reference to exemplary embodiments and the accompanying drawings, the present invention is not limited thereto, but may be variously modified and altered by those skilled in the art to which the present invention pertains without departing from the spirit and scope of the present invention claimed in the following claims.

What is claimed is:

1. An optical assembly comprising:
a case provided with a first optical path, formed therein, which passes light irradiated from a first light source, and a second optical path, formed therein, which communicates with a side of the first optical path and introduces the light irradiated from a second light source in a different direction from the first light source into the first optical path; and
a beam splitter provided in the first optical path, divides the first optical path into an irradiation area in a front side and an incident area in a rear side, maintains a traveling direction with respect to the light irradiated from the first light source, and changes the traveling direction of the light irradiated from the second light source so that the light irradiated from the second light source can travel in parallel to the light irradiated from the first light source,
wherein the first optical path is formed in such a manner that a centerline of the irradiation area and a centerline of the incidence area are not parallel to each other.

2. The optical assembly of claim 1, wherein the centerline of the irradiation area and the centerline of the incidence area are laterally spaced by a preset correction distance (x) so that a traveling trace of the light irradiated from the first light source and a traveling trace of the light irradiated from the second light source coincide with each other in the irradiation area.

3. The optical assembly of claim 2, wherein the correction distance is calculated by following equation $$x = \frac{d_2}{\cos\theta_2} \cdot \cos(\theta_2 + 90 - \theta_3)$$

(d2: a thickness of beam splitter)
(θ2: an angle between a first vertical line passing through a first contact point where the light irradiated from the first light source meets a rear surface of the beam splitter and perpendicular to the rear surface of the beam splitter and a trace of the light, irradiated from the first light source, travelling in the beam splitter)
(θ3: an angle between a second vertical line passing through a second contact point where the light irradiated from the first light source meets a front surface of the beam splitter and perpendicular to the front surface of the beam splitter and a trace of the light, irradiated from the first light source, travelling in the beam splitter).

4. The optical assembly of claim 1, wherein an insertion groove corresponding to a cross-sectional shape of the beam splitter is formed on an inner circumferential surface of the first optical path formed in the case, so that the beam splitter is inserted and fixed to the insertion groove.

5. The optical assembly of claim 4, wherein the case includes an upper case and a lower case divided to bisect the first optical path, the second optical path, and the insertion groove.

6. The optical assembly of claim 1, wherein the case comprises a first lens coupling unit formed in a front end of the first optical path and a second lens coupling unit formed in a rear end of the first optical path, further comprising a first lens coupled to the first lens coupling unit and a second lens coupled to the second lens coupling unit.

7. A light source device for endoscope, the device comprising the optical assembly according to claim 1.

* * * * *